US008106259B2

(12) United States Patent
Beetham et al.

(10) Patent No.: US 8,106,259 B2
(45) Date of Patent: Jan. 31, 2012

(54) COMPOSITIONS AND METHODS FOR PLANT GENETIC MODIFICATION

(75) Inventors: Peter R. Beetham, Carlsbad, CA (US); Keith A. Walker, San Diego, CA (US); Patricia L. Avissar, New Brunswick, NJ (US)

(73) Assignee: Cibus US LLC, San Diego, CA (US)

( * ) Notice: Subject to any disclaimer, the term of this patent is extended or adjusted under 35 U.S.C. 154(b) by 0 days.

(21) Appl. No.: 12/463,891

(22) Filed: May 11, 2009

(65) Prior Publication Data

US 2010/0203639 A1    Aug. 12, 2010

Related U.S. Application Data

(63) Continuation of application No. 11/338,586, filed on Jan. 24, 2006, now abandoned, which is a continuation of application No. 09/680,858, filed on Oct. 6, 2000, now abandoned.

(60) Provisional application No. 60/158,033, filed on Oct. 7, 1999, provisional application No. 60/173,555, filed on Dec. 30, 1999.

(51) Int. Cl.
   *C12N 15/82* (2006.01)
(52) U.S. Cl. ........................................ 800/295; 800/306
(58) Field of Classification Search ........................ None
   See application file for complete search history.

(56) References Cited

U.S. PATENT DOCUMENTS

| 5,629,183 A | 5/1997 | Saunders et al. | |
| 5,731,181 A * | 3/1998 | Kmiec | 435/6 |

FOREIGN PATENT DOCUMENTS

| WO | WO 93/21335 | 10/1993 |
| WO | WO-93/21335 | 10/1993 |
| WO | WO 95/15972 | 6/1995 |
| WO | WO-95/15972 | 6/1995 |
| WO | WO-97/48714 | 12/1997 |
| WO | WO 97/48714 | 12/1997 |
| WO | WO-98/54330 | 12/1998 |
| WO | WO 98/54330 | * 12/1998 |
| WO | WO-99/07865 | 2/1999 |
| WO | WO 99/07865 | 2/1999 |

OTHER PUBLICATIONS

Fennell et al 1992, Plant Cell Reports 11:567-570.*
Fukuoka et al Mar. 1998, Plant Cell Reports 17: 323-328.*
Swanson, E. B., et al. "Microspore mutagenesis and selection: Canola plants with field tolerance to the imidazolinones", *TAG Theoretical and Applied Genetics*, Oct. 1989, pp. 525-530, vol. 78, No. 4.
Liang, I., et al. "Optimizing the delivery systems of chimeric RNA-DNA oligonucleotides-beyond general oligonucleotide transfer", *Eur. J. Biochem.*, 2002, pp. 5753-5758, vol. 269.
Beetham, P. R., et al. "A tool for functional plant genomics: Chimeric RNA/DNA oligonucleotides cause in vivo gene-specific mutations", *Proc. Natl. Acad. Sci. USA*, Jul. 1999, pp. 8774-8778, vol. 96.

Zhu, T., et al. "Targeted manipulation of maize genes in vivo using chimeric RNA/DNA oligonucleotides", *Proc. Natl. Acad. Sci. USA*, Jul. 1999, pp. 8768-8773, vol. 96.
Kochevenko, A., et al. "Chimeric RNA/DNA oligonucleotide-based site-specific modification of the tobacco acetolactate syntase gene", *Plant Physiology*, May 2003, pp. 174-184, vol. 132.
Souvre, A., et al. "Transformation of rape (*Brassica Napes L.*) through the haploid embryogenesis pathway", *ACTA SOCIETATIS BOTANICORUM POLONIAE*, 1996, pp. 194-195, vol. 65, Nos. 1-2.
Fukuoka, H., et al. "Direct gene delivery into isolated microspores of rapeseed (*Brassica napus L.*) and the production of fertile transgenic plants", *Plant Cell Reports*, Mar. 1998, pp. 323-328, vol. 17, No. 5.
Qing, Y. A., et al. "Biolistic transformation of haploid isolated microspores of barley", *Genome*, 1997, pp. 570-581, vol. 40, No. 4, Abstract Only.
Jardinaud, M-F., et al. "Transient GUS gene expression in *Brassica napus* electroporated microspores", Plant Science (Limerick), 1993, pp. 177-184, vol. 93, Nos. 1-2.
Fennell, A., et al. "Electroporation and PEG delivery of DNA into maize microspores", *Plant Cell Reports*, 1992, pp. 567-570, vol. 11.
Hohn, B., et al. "Gene therapy in plants", *Proc. Natl. Acad. Sci. USA*, Jul. 1999, pp. 83218323, vol. 96.
Beetham, P.R., et al, "A tool for functional plant genomics: Chimeric RNA/DNA oligonucleotides cause in vivo gene-specific mutations", Proc. Natl. Acad. Sci, USA, Jul. 1999, pp. 8774-8778, vol. 96.
Fennell., A., et al. "Electroporation and PEG delivery of DNA into maize microspores", Plant Cell Reports, 1992, pp. 567-570, vol. 11.
Fukuoka, H., et al. "Direct gene delivery into isolated microspores of rapeseed (Brassica napus L.) and the production of fertile transgenic plants", Plant Cell Reports, Mar. 1998, pp. 323-328, vol. 17, No. 5.
Hohn, B., et al. "Gene therapy in plants", Proc. Natl. Acad. Sci. USA, Jul. 1999, pp. 831-8323, vol. 96.
Jardinaud, M.F., et al. "Transient GUS gene expression in *Brassica napus* electroporated microspores", Plant Science (LIMERICK), 1993, pp. 177-184, vol. 93, Nos. 1-2. Kochevenko, A., et al. "Chimeric RNA/DNA oligonculeotide-based site specific modification of the tobacco acetolactate syntase gene", Plant Physiology, May 2003, pp. 174-184, vol. 132.
Liang, I., et al. "Optimizing the delivery systems of chimeric RNA-DNA oligonucleotides-beyond general oligonucleotide transfer", Eur. J. Biochem., 2002, pp. 5753-5758, vol. 269.
PCT International Search Report for PCT/US00/27870 dated Sep. 28, 2001 (6 pages).
Qing, Y., et al. Biolistic transformation of the haploid isolated microspores of barley (Hordelium vulgare L.), Genome 40(4):570-581 Abstract Only, 1997.
Souvre, A., et al. "Transformation of rape (Brassica Napus L.) through the haploid embryogenesis pathway", ACTA SOCIETATIS BOTANICORUM POLONIAE, 1996, pp. 194-195, vol. 65, Nos. 1-2.
Swanson, E.B, et al, "Microscope mutagenesis and selection: Canola plants with field tolerance to the imidazolinones", TAG Theoretical and Applied Genetics, Oct. 1989, pp. 525-530, vol. 78, No. 4.
Zhu, T., et al. "Targeted manipulation of maize genes in vivo using chimeric RNA/DNA oligonucleotides", Proc. Natl. Acad. Sci. USA, Jul. 1999, pp. 8768-8773, vol. 96.

* cited by examiner

*Primary Examiner* — David H Kruse
(74) *Attorney, Agent, or Firm* — Foley & Lardner LLP; Stephen E. Reiter

(57) ABSTRACT

Mixed duplex oligonucleotides (MDON) are used to effect site-specific genetic alterations in a target DNA sequence of a plant. The MDON are introduced by electroporation into microspores. Thereafter, plants having a desired genetic alteration are produced by germinating the microspores.

6 Claims, No Drawings

SEQUENCE LISTING

<160> NUMBER OF SEQ ID NOS: 14

<210> SEQ ID NO 1
<211> LENGTH: 68
<212> TYPE: DNA
<213> ORGANISM: Artificial Sequence
<220> FEATURE:
<223> OTHER INFORMATION: Mixed duplex oligonucleotide (MDON) ALS-1

<400> SEQUENCE: 1
caggtcaagt gcaacgtagg atgattttta ucaaccuacg ttgcacuuga ccuggcgcgt      60
tttcgcgc                                                              68

<210> SEQ ID NO 2
<211> LENGTH: 68
<212> TYPE: DNA
<213> ORGANISM: Artificial Sequence
<220> FEATURE:
<223> OTHER INFORMATION: Mixed duplex oligonucleotide (MDON) ALS-2

<400> SEQUENCE: 2
caggtcaagt gctacgtagg atgattttta ucaaccuacg tagcacuuga ccuggcgcgt      60
tttcgcgc                                                              68

<210> SEQ ID NO 3
<211> LENGTH: 24
<212> TYPE: DNA
<213> ORGANISM: Artificial Sequence
<220> FEATURE:
<223> OTHER INFORMATION: Green Fluorescence Protein (GFP)

<400> SEQUENCE: 3
atggtgagca agggcgagga gctg                                            24

<210> SEQ ID NO 4
<211> LENGTH: 67
<212> TYPE: DNA
<213> ORGANISM: Artificial Sequence
<220> FEATURE:
<223> OTHER INFORMATION: Mixed duplex oligonucleotide (MDON) GFP-1

<400> SEQUENCE: 4
gtgagcaagg gcgaggagct gttcattttu gaacagcucc tcgccuugcu cacgcgcgtt      60
ttcgcgc                                                               67

<210> SEQ ID NO 5
<211> LENGTH: 68
<212> TYPE: DNA
<213> ORGANISM: Artificial Sequence
<220> FEATURE:
<223> OTHER INFORMATION: Mixed duplex oligonucleotide (MDON) GFP-2

<400> SEQUENCE: 5
tgagcaaggg ctcggagctg ttcacttttg ugaacagcuc cgagcccuug cucagcgcgt      60

```
tttcgcgc                                                             68

<210> SEQ ID NO 6
<211> LENGTH: 68
<212> TYPE: DNA
<213> ORGANISM: Artificial Sequence
<220> FEATURE:
<223> OTHER INFORMATION: Tobacco acetolactate synthase mixed duplex
      oligonucleotide (MDON) ALS-1

<400> SEQUENCE: 6
caggtcaagt gcaacgtagg atgattttta ucauccuacg ttgcacuuga ccuggcgcgt    60
tttcgcgc                                                             68

<210> SEQ ID NO 7
<211> LENGTH: 67
<212> TYPE: DNA
<213> ORGANISM: Artificial Sequence
<220> FEATURE:
<223> OTHER INFORMATION: Tobacco acetolactate synthase mixed duplex
      oligonucleotide (MDON) ALS-2

<400> SEQUENCE: 7
caggtcaagt gctacgtagg atgattttta ucauccuact agcacuugac cuggcgcgtt    60
ttcgcgc                                                              67

<210> SEQ ID NO 8
<211> LENGTH: 68
<212> TYPE: DNA
<213> ORGANISM: Artificial Sequence
<220> FEATURE:
<223> OTHER INFORMATION: Tobacco green fluorescent protein mixed duplex
      oligonucleotide (MDON) GFP-1

<400> SEQUENCE: 8
gtgagcaagg gcgaggagct gttcattttu gaacagcucc tcgcccuugc ucacgcgcgt    60
tttcgcgc                                                             68

<210> SEQ ID NO 9
<211> LENGTH: 68
<212> TYPE: DNA
<213> ORGANISM: Artificial sequence
<220> FEATURE:
<223> OTHER INFORMATION: Tobacco green fluorescent protein mixed duplex
      oligonucleotide (MDON) GFP-2

<400> SEQUENCE: 9
tgagcaaggg ctcggagctg ttcacttttg ugaacagcuc cgagcccuug cucagcgcgt    60
tttcgcgc                                                             68

<210> SEQ ID NO 10
<211> LENGTH: 68
<212> TYPE: DNA
<213> ORGANISM: Artificial sequence
<220> FEATURE:
<223> OTHER INFORMATION: Arabidopsis thaliana phosphoribosylanthranilate
      transferase mixed duplex oligonucleotide (MDON) PAT4

<400> SEQUENCE: 10
ctgcttgtgg aagtgctgat gtacttttta guacaucagc acttccacaa gcaggcgcgt    60
tttcgcgc                                                             68

<210> SEQ ID NO 11
<211> LENGTH: 68
```

```
<212> TYPE: DNA
<213> ORGANISM: Artificial Sequence
<220> FEATURE:
<223> OTHER INFORMATION: Arabidopsis thaliana phosphoribosylanthranilate
      transferase mixed duplex oligonucleotide (MDON) PAT3

<400> SEQUENCE: 11
ctgcttgtgg aaatgctgat gtacttttta guacaucagc atttccacaa gcaggcgcgt      60
tttcgcgc                                                              68

<210> SEQ ID NO 12
<211> LENGTH: 68
<212> TYPE: DNA
<213> ORGANISM: Artificial sequence
<220> FEATURE:
<223> OTHER INFORMATION: Arabidopsis thaliana fatty acid desaturase
      mixed duplex oligonucleotide (MDON) ATFAD2/217

<400> SEQUENCE: 12
cgctcccatc tagaatgacc gagaattttu ucucggucat tctagauggg agcggcgcgt      60
tttcgcgc                                                              68

<210> SEQ ID NO 13
<211> LENGTH: 68
<212> TYPE: DNA
<213> ORGANISM: Artificial Sequence
<220> FEATURE:
<223> OTHER INFORMATION: Tobacco putrescine N-methyltransferase mixed
      duplex oligonucleotide (MDON)

<400> SEQUENCE: 13
aatggcactt cttaacacct caacgttttc guugaggugt taagaagugc cauugcgcgt      60
tttcgcgc                                                              68

<210> SEQ ID NO 14
<211> LENGTH: 67
<212> TYPE: DNA
<213> ORGANISM: Artificial Sequence
<220> FEATURE:
<223> OTHER INFORMATION: Canola AHAS3 gene S635N mixed duplex
      oligonucleotide (MDON)

<400> SEQUENCE: 14
cgatgatccc aagtggtggc actttttta agugccacca cttgggauca ucggcgcgtt      60
ttcgcgc                                                               67
```

COMPOSITIONS AND METHODS FOR PLANT GENETIC MODIFICATION

CROSS-REFERENCE TO RELATED APPLICATIONS

The present application is a continuation application of U.S. patent application Ser. No. 11/338,586, filed Jan. 24, 2006 now abandoned, which is a continuation of U.S. application Ser. No. 09/680,858, filed Oct. 6, 2000 now abandoned; which claims the benefit of U.S. Provisional Application Ser. No. 60/158,033, filed Oct. 7, 1999 and U.S. Provisional Application Ser. No. 60/173,555, filed Dec. 30, 1999, which are incorporated herein by reference in their entirety.

FIELD OF THE INVENTION

The present invention relates to compositions and methods for plant genetic modification, specifically for making specific modifications in a target gene through the use of duplex oligonucleotides having a mixture of RNA-like nucleotides and DNA-like nucleotides, hereafter referred to as "mixed duplex oligonucleotides" or MDON.

A used herein, the term MDON is synonymous with the terms "chimeric mutation vector," "chimeric repair vector" and "chimeraplast" which are used elsewhere in the literature.

BACKGROUND OF THE INVENTION

Recombinant DNA technology enables the production of genetically altered plants through the introduction of preconstructed exogenous genes or "transgenes" in random, atopic positions. By contrast, the present invention makes it possible to make a specific alteration of a specific target gene of a plant through the use of MDON. We have developed improved methods of introducing MDON in to plant cells in order to achieve specific modifications of a target gene while improving the recovery of viable, fertile plants that have the desired genetic modifications.

Use of MDON to Effect Specific Genetic Alterations

Mixed duplex oligonucleotides (MDON) and their use to effect genetic changes in eukaryotic cells are described in U.S. Pat. No. 5,565,350 to Kmiec (Kmiec I). Kmiec I discloses inter alia MDON having two strands, the first strand containing two segments of at least eight RNA-like nucleotides that are separated by a third segment of from 4 to about 50 DNA-like nucleotides, termed an "interposed DNA segment." The nucleotides of the first strand are base paired to DNA-like nucleotides of a second strand.

The first and second strands are additionally linked by a segment of single stranded nucleotides, so that the first and second strands are parts of a single oligonucleotide chain. Kmiec I further teaches a method for introducing specific genetic alterations into a target gene. According to Kmiec I, the sequences of the RNA segments are selected to be homologous, i.e., identical, to the sequence of a first and a second fragment of the target gene. The sequence of the interposed DNA segment is homologous with the sequence of the target gene between the first and second fragment except for a region of difference, termed the "heterologous region." The heterologous region can effect an insertion or deletion or can contain one or more bases that are mismatched with the sequence of target gene so as to effect a substitution. According to Kmiec I, the sequence of the target gene is altered as directed by the heterologous region, such that the target gene becomes homologous with the sequence of the MDON. Kmiec I specifically teaches that nucleotides that contain ribose and 2'-O-methylribose, i.e., 2'-methoxyribose, can be used in MDON and that naturally-occurring deoxyribose-containing nucleotides can be used as DNA-like nucleotides.

U.S. Pat. No. 5,731,181 (Kmiec II), discusses the use of MDON to effect genetic changes in plant cells and provides further examples of analogs and derivatives of RNA-like and DNA-like nucleotides that can be used to effect genetic changes in specific target genes.

Scientific publications disclosing uses of MDON having interposed DNA segments include Yoon, et al., 1996, *Proc. Natl. Acad. Sci.* 93:2071-2076 and Cole-Straus, A. et al., 1996, *Science* 273:1386-1389. The rates of mutation achieved in these studies ranges to as high as about one cell in ten using liposome-mediated delivery. However, these publications do not disclose that MDON can be used to make genetic changes in plant cells.

Introduction of MDON into Plant Cells using Electroporation and Microprojectile Bombardment. Kmiec I and II discuss the use of electroporation for introduction of MDON into plant protoplasts. The regeneration of fertile plants from protoplast cultures has been reported for certain species of dicotyledonous plants, e.g., *Nicotiana tobacum* (tobacco), U.S. Pat. No. 5,231,019 and Fromm, M. E., et al., 1988, Nature 312, 791, and soybean variety *Glycine max*, WO 92/17598 to Widholm, J. M. However, despite the reports of isolated successes using non-transformed cells (Prioli, L. M., et al., Bio/Technology 7, 589; Shillito, R. D., et al., 1989, Bio/Technology 7, 581), the regeneration of fertile monocotyledonous plants from transformed protoplast cultures is not regarded as obtainable with application of routine skill. Frequently, transformed protoplasts of monocotyledonous plants result in non-regenerable tissue or, if the tissue is regenerated, the resultant plant is infertile.

U.S. Pat. Nos. 4,945,050, 5,100,792 and 5,204,253 concern microprojectile bombardment, the delivery of plasmids into intact plant cells by adhering the plasmid to a microparticle that is ballistically propelled across the cell wall, hereafter "biolistically transformed" cell. For example U.S. Pat. No. 5,489,520 describes the regeneration of a fertile maize plant from a biolistically transformed cell.

U.S. Pat. No. 5,302,523 discusses the introduction of plasmid DNA into suspensions of plant cells having intact cell walls through the use of silicon carbide fibers that pierce the cell wall.

U.S. Pat. No. 5,384,253 discusses the use of a combination of endopectin lyase (E.C. 3.2.1.15) and endopolygalacturonase (E.C. 4.2.2.3) to generate transformation-competent cells that can be more readily regenerated into fertile plants than true protoplasts. However, the technique is reported to be useful only for F1 cell lines from the cross of line A188×line B73.

Mutagenesis of Plant Genes to Confer Herbicide Tolerance. U.S. Pat. No. 4,535,060 discusses the production of herbicide-tolerant plants by introducing mutations into plant genes that encode certain enzymes that when mutated are more resistant to a competitive inhibitor of the enzymes that acts as an herbicide. However, results from these techniques have been limited, and more reliable methods with wider applicability are needed.

The possibility of gene replacement in plants by homologous recombination (the Smithies-Capecchi technique) has been discussed, but this technique has not been successfully applied to plants.

Imidazolinone resistance can be conferred on plants by mutations in the aminohydroxy acid synthase (AHAS) gene. This is exemplified by "Smart Canola," which has a mutation in AHAS 1 gene at amino acid position 635 (also known as PM1) and a mutation in AHAS 3 at the same amino acid position (PM2). The PM2 mutation also confers resistance to an additional family of herbicides.

SUMMARY OF THE INVENTION

The present invention provides new compositions and methods for plant genetic modification in which an MDON is electroporated into a microspore or population thereof. The microspore is subsequently cultured to promote the development of a somatic embryo (haploid or double-haploid, as in the case of *Brassica napus*, due to the allotetraploid nature of the species) from which a mature plant can be produced that has a desired genetic modification in a target DNA sequence caused by the MDON. This approach can be used for the genetic modification of any plant for which microspores can be isolated and for which microspore culture is possible, and can be used to modify any target DNA sequence, including coding and non-coding sequences.

The use of microspores as a target tissue rather than other plant tissues is advantageous for a number of reasons. Production of haploid or double-haploid plants from genetically modified microspores enables the production of completely homozygous breeding lines in a much shorter time compared to traditional plant breeding methods. In addition, this approach eliminates the need for initiation, selection and maintenance of embryogenic cells or callus cultures that provide a source of protoplasts for electroporation or polyethylene glycol-mediated transformation.

Thus, according to one embodiment of the invention, methods are provided for mutating a target DNA sequence of a plant that include the steps of (1) electroporating into a microspore of the plant a recombinagenic oligonucleobase that contains a first homologous region that has a sequence identical to the sequence of at least 6 base pairs of a first fragment of the target DNA sequence and a second homologous region which has a sequence identical to the sequence of at least 6 base pairs of a second fragment of the target DNA sequence, and an intervening region which contains at least 1 nucleobase heterologous to the target DNA sequence, which intervening region connects the first homologous region and the second homologous region; (2) culturing the microspore to produce an embryo; and (3) producing from the embryo a plant having a mutation located between the first and second fragments of the target DNA sequence, e.g., by culturing the microspore to produce a somatic embryo and regenerating the plant from the embryo. In various embodiments of the invention, the recombinagenic oligonucleobase is an MDON and each of the homologous regions contains an RNA segment of at least 6 RNA-type nucleotides; the intervening region is at least 3 nucleotides in length; the first and or second RNA segment contains at least 8 contiguous 2'-substituted ribonucleotides. Preferably, the sequence of the mutated target DNA sequence is homologous with the sequence of the MDON. The present invention also encompasses seeds and plants and their progeny produced by such methods.

The methods of the invention are applicable to mutagenesis of any target DNA sequence. Examples include, but are not limited to, genes encoding ALS genes, psbA, threonine dehydratase, dihydrodipicolinate synthase, acetolactate synthase, green fluorescent protein, phosphoribosylanthranilate transferase, fatty acid desaturase, putrescine N-methyltransferase, acid invertase, UDP-glucose pyrophosphorylase, polyphenol oxidase, O-methyl transferase, cinnamyl alcohol dehydrogenase, etr-1 or a homolog thereof, ACC synthase and ACC oxidase, the S14/rp59 gene, EPSP synthase, and protoporphyrogen oxidase, for example. The methods of the invention are also applicable to a wide variety of plants from which microspores can be isolated and cultured, including corn, soybean, wheat, rice, cotton, and Brassicaceae, including canola (*Brassica napus*, *Brassica rapa*, *Brassica oleracea*, and *Brassica juncea*).

According to another embodiment of the invention, methods are provided for making a localized, non-selectable mutation in a target DNA sequence of a plant comprising the steps of: (1) introducing into a population of microspores of the plant a mixture comprising a first recombinagenic oligonucleobase and a second recombinagenic oligonucleobase wherein (i) the first recombinagenic oligonucleobase contains a first homologous region which has a sequence identical to the sequence of at least 6 base pairs of a first fragment of a first target DNA sequence and a second homologous region which has a sequence identical to the sequence of at least 6 base pairs of a second fragment of the first target DNA sequence, and an intervening region which contains at least 1 nucleobase heterologous to the target DNA sequence, which intervening region connects the first homologous region and the second homologous region, and (ii) the second recombinagenic oligonucleobase contains a first homologous region which has a sequence identical to the sequence of at least 6 base pairs of a first fragment of a second target DNA sequence and a second homologous region which has a sequence identical to the sequence of at least 6 base pairs of a second fragment of the second target DNA sequence, and an intervening region which contains at least 1 nucleobase heterologous to the target DNA sequence, which intervening region connects the first homologous region and the second homologous region; (2) selecting microspores from the population having a selectable mutation located between the first and the second fragments of the first target DNA sequence from the population; and (3) identifying selected microspores having a nonselectable mutation located between the first fragment and the second fragment of the second target DNA sequence. Microspores having a non-selectable mutation located between the first fragment and the second fragment of the second target DNA sequence can be cultured to produce an embryo, and plants can be produced from such embryos.

According to another embodiment of the invention, plants or seeds are provided that have a point mutation in a DNA sequence that is in its wild-type genetic position. Such DNA sequences include those selected from the group consisting of the genes encoding acid invertase, UDP-glucose pyrophosphorylase, polyphenol oxidase, O-methyl transferase, cinnamyl alcohol dehydrogenase, ACC synthase, ACC oxidase, etr-1 or a homolog of etr-1, EPSP synthase, and protoporphyrogen oxidase. Since it is possible to modify DNA at the target DNA sequence without affecting surrounding genomic DNA sequences, genomic DNA within 23 KB, 40 KB, or even 100 KB or more of the point mutation remains identical to the sequence of the wild type DNA. Such methods are useful for introducing stop codons or frameshift mutations into a target DNA sequence, for example. The point mutations introduced in this fashion may be single basepair mutations or may alter more than a single basepair. According to another embodiment of the invention, in addition to having a point mutation in the first DNA sequence, such plants or seeds may also have a selectable point mutation in a second DNA sequence. Again, the sequence of genomic DNA adjacent the selectable point mutation (e.g., within 23, 40, or 100 KB of the selectable point mutation) has the same sequence as the wild type DNA.

According to another embodiment of the invention, methods are provided for altering at least one base of a target DNA sequence of a plant comprising: (1) providing a microspore of the plant; (2) introducing a mixed duplex oligonucleotide into the microspore, for example by electroporation; and (3) producing a plant from the microspore having an alteration in at least one base in a target DNA sequence caused by the mixed duplex oligonucleotide.

According to other embodiments of the invention, various compositions of matter are provided, including, for example, plant microspores comprising a mixed duplex oligonucleotide and compositions of matter comprising or including a plurality of plant microspores and an aqueous solution comprising a mixed duplex oligonucleotide that is suitable for electroporation of the mixed duplex oligonucleotide into the microspores.

The invention further encompasses the culture of microspores mutated according to the foregoing embodiments of the invention so as to obtain a plant that produces seeds, henceforth a "fertile plant," and the production of seeds and additional plants from such a fertile plant.

The invention further encompasses fertile plants having novel characteristics that are produced by the methods of the invention.

It should be noted that the term "comprising" as used herein has the meaning generally given under U.S. patent law.

DETAILED DESCRIPTION OF THE INVENTION

We have discovered improved methods for producing plants having desirable mutations in DNA sequences in their genetic material (including nuclear, plastid, and mitochondrial genomes) by electroporation of MDON into microspores of the plant. These methods are useful for altering any target DNA sequence in any plant for which microspore isolation and culture is possible.

As one example, canola plants with an increased tolerance to herbicides of the chlorosulphuron and imidazolinone families can be produced by electroporating into canola microspores an MDON that introduces mutations into the aminohydroxy acid synthase (AHAS) gene sequence, thereby increasing the resistance of AHAS enzyme encoded by the mutated gene to such herbicides, and culturing the microspores to produce embryos from which plants can be produced by standard techniques. As one example, a mutation of the AHAS 3 gene at position 557 (Trp557Leu) confers resistance to imidazolinones (Rutledge et al., Mol. Gen. Genet. 229:31-40, 1991; Ouellet et al., Plant J. 2:321-330, 1992; Hattori et al., Mol. Gen. Genet. 246:419-425, 1995).

The methods of the present invention can be used not only to alter protein-coding sequences, but also non-coding sequences such as promoter sequences, thereby modifying gene expression.

Recombinagenic Oligonucleobases and Mixed Duplex Oligonucleotides

The invention can be practiced with MDON having the conformations and chemistries described in Kmiec I or in Kmiec II, which are hereby incorporated by reference. The MDON of Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Commonly assigned U.S. patent application Ser. No. 09/078,063, filed May 12, 1998, and Ser. No. 09/078,064, filed May 12, 1998, which are each hereby incorporated in their entirety, disclose additional molecules that can be used for the present invention. The term "recombinagenic oligonucleobase" is used herein to denote the molecules that can be used in the present invention. Recombinagenic oligonucleobases include MDON, non-nucleotide containing molecules taught in Kmiec II and the molecules taught in the above noted commonly assigned patent applications.

According to one embodiment of the invention, the RNA-type nucleotides of the MDON are made Rnase-resistant by replacing the 2'-hydroxyl with a fluoro, chloro or bromo functionality or by placing a substituent on the 2'-O, Suitable substituents include the substituents taught by the Kmiec II, $C_{1-6}$ alkane. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-substituted nucleotide that is linked to other nucleotides of a MDON by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

A particular embodiment of the invention comprises MDON that are linked solely by unsubstituted phosphodiester bonds. Alternatively embodiments comprise linkage by substituted phosphodiesters, phosphodiester derivatives and non-phosphorus-based linkages as taught by Kmiec II. A further particular embodiment comprises MDON wherein each RNA-type nucleotide is a 2'-substituted nucleotide. Particular preferred embodiments of 2'-substituted ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. In more preferred embodiments of 2'-substituted ribonucleotides are 2'-fluoro, 2'-methoxy, 2'-methoxyethyloxy, and 2'-allyloxy substituted nucleotides. In one embodiment the MDON oligomer is linked by unsubstituted phosphodiester bonds.

Although MDON having only a single type of 2'-substituted RNA-type nucleotide are more conveniently synthesized, the invention can be practiced with MDON having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The MDON of the invention preferably have fewer than 100 nucleotides and more preferably fewer than 85 nucleotides, but more than 50 nucleotides. The first and second strands are Watson-Crick base paired. In one embodiment the strands of the MDON are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the MDON may differ from the sequence of the target gene only by the deletion of one, two, three, or five or fewer nucleotides from the MDON. The length and position of the heterologous region is, in this case, deemed to be the length of the deletion, even though no nucleotides of the MDON are within the heterologous region. The distance between the fragments of the target gene that are complementary to the two homologous regions is identically the length of the heterologous region when a substitution or substitutions is intended. When the heterologous region contains an insertion, the homologous regions are thereby separated in the MDON farther than their complementary homologous fragments are in the gene, and the converse is applicable when the heterologous region encodes a deletion.

The RNA segments of the MDON are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a MDON is termed a "mutator segment."

Commonly assigned U.S. patent application Ser. No. 09/078,063, filed May 12, 1998, and Ser. No. 09/078,064, filed May 12, 1998, disclose a type of duplex recombinagenic oligonucleobase in which a strand has a sequence that is identical to that of the target gene and only the sequence of the "complementary" strand contains a heterologous region. This configuration results in one or more mismatched bases or a "heteroduplex" structure. The heterologous region of the heteroduplex recombinagenic oligonucleobases that are useful in the present invention is located in the strand that contains the deoxynucleotides. In one embodiment, the heterologous region is located on the strand that contains the 5' terminal nucleotide.

The Location and Type of Mutation Introduced by a MDON

Frequently, the design of the MDON for use in plant cells must be modified from the designs taught in Kmiec I and II. In mammalian and yeast cells, the genetic alteration introduced by a MDON that differs from the target gene at one position is the replacement of the nucleotide in the target gene at the mismatched position by a nucleotide complementary to the nucleotide of the MDON at the mismatched position. By contrast, in plant cells there can be an alteration of the nucleotide one base 5' to the mismatched position on the strand that is complementary to the strand that contains the DNA mutator segment. The nucleotide of the target gene is replaced by a nucleotide complementary to the nucleotide of the DNA mutator segment at the mismatched position. Consequently, the mutated target gene differs from the MDON at two positions.

The mutations introduced into the target gene by a MDON are located between the regions of the target gene that are homologous with the ribonucleotide portion of the homology regions of the MDON, henceforth the "RNA segments." The specific mutation that is introduced depends upon the sequence of the heterologous region. An insertion or deletion in the target gene can be introduced by using a heterologous region that contains an insertion or deletion, respectively. A substitution in the target gene can be obtained by using a MDON having a mismatch in the heterologous region of the MDON. In the most frequent embodiments, the mismatch will convert the existing base of the target gene into the base that is complementary to the mismatched base of the MDON. The location of the substitution in the target gene can be either at the position that corresponds to the mismatch or, more frequently, the substitution will be located at the position on the t strand immediately 5' to the position of the mismatch, i.e., complementary to the position of the MDON immediately 3' of the mismatched base of the MDON.

The relative frequency of each location of the mismatch-caused substitution will be characteristic of a given gene and cell type. Thus, those skilled in the art will appreciate that a preliminary study to determine the location of substitutions in the gene of particular interest is generally indicated, when the location of the substitution is critical to the practice of the invention.

The foregoing techniques can be adapted for use with recombinagenic oligonucleobases other than MDON.

Introduction of MDON into Microspores by Electroporation

Upon release of the tetrad, the microspore is uninucleate and thin-walled. It begins to enlarge and develops a germpore before the exine forms. A microspore at this stage is potentially more amenable to transformation with exogenous DNA than other plant cells. In addition, microspore development can be altered in vitro to produce either haploid embryos or embryogenic callus that can be regenerated into plants (Coumans et al., *Plant Cell Rep.* 7:618-621, 1989; Datta et al., *Plant Sci.* 67:83-88, 1990; Maheshwari et al., *Am. J. Bot.* 69:865-879, 1982; Schaeffer, *Adv. In Cell Culture* 7:161-182, 1989; Swanson et al., *Plant Cell Rep.* 6:94-97, 1987). Thus transformed microspores could be grown directly into haploid plants or dihaploid fertile plants upon chromosome doubling (Wan et al., 1989).

The methods of the present invention can be used with any plant species for which microspore culture is possible, including but not limited to plants in the families Graminae, Leguminoceae, Cruciferaceae, Solanaceae, Cucurbitaceae, Rosaceae, Poaceae, Lilaceae, Rutaceae, Vitaceae, including such species as corn (*Zea mays*), wheat (*Triticum aestivum*), rice (*Oryza sativa*), oats, barley, canola (*Brassica napus, Brassica rapa, Brassica oleracea*, and *Brassica juncea*), cotton (*Gossypium hirsuitum* L.), various legume species (e.g., soybean [*Glycine max*], pea [*Pisum sativum*], etc.), grapes [*Vitis vinifera*], and a host of other important crop plants. Microspore embryogenesis, both from anther and microspore culture, has been described in more than 170 species, belonging to 68 genera and 28 families of dicotyledons and monocotyledons (Raghavan, *Embryogenesis in Angiosperms: A Developmental and Experimental Study*, Cambridge University Press, Cambridge, England, 1986; Rhagavan, *Cell Differentiation* 21:213-226, 1987; Raemakers et al., *Euphytica* 81:93-107, 1995). For a detailed discussion of microspore isolation, culture, and regeneration of double haploid plants from microspore-derived embryos [MDE] in *Brassica napus* L., see Nehlin, *The Use of Rapeseed (Brassica napus L.) Microspores as a Tool for Biotechnological Applications*, doctoral thesis, Swedish. University of Agricultural Sciences, Uppsala, Sweden, 1999; also Nehlin et al., *Plant Sci.* 111: 219-227, 1995, and Nehlin et al., *Plant Sci,* 111:219-227; 1995). Chromosome-doubling from microspore or anther culture is a well-established technique for production of double-haploid homozogous plant lines in several crops (Heberle-Bors et al., *In vitro pollen cultures: Progress and perspectives.* In: *Pollen Biotechnology. Gene expression and allergen characterization*, vol. 85-109, ed. Mohapatra, S. S, and Knox, R. B., Chapman and Hall, New York, 1996).

Microspore electroporation methods are described in Jardinaud et al., *Plant Sci.* 93:177-184, 1993, and Fennell and Hauptman, *Plant Cell Reports* 11:567-570, 1992. Methods for electroporation of MDON into plant protoplasts, such as the procedure discussed in detail in the Examples, can be used for introduction of MDON into microspores.

The term "plant" is used herein to mean any differentiated multicellular organism capable of photosynthesis, including, but not limited to, monocotyledonous plants, dicotyledonous plants, and gymnosperms.

The Introduction of Mutations Using MDON

The invention can be used to effect genetic changes, herein "transmutate," in plant cells. In an embodiment the plant cells have cell walls, i.e., are other than protoplasts.

The use of MDON to transmutate plant cells can be facilitated by co-introducing a trait that allows for the ready differentiation and separation of cells (hereafter "selection") into which MDON have been introduced from those that have not. In one embodiment of the invention the selection is performed by forming a mixture of MDON and a plasmid that causes the transient expression of a gene that confers a selectable trait, i.e., one that permits survival under certain conditions, e.g., a kanamycin resistance gene. Under these circumstances elimination of cells lacking the selectable trait removes the cells into which MDON were not introduced. The use of a transient expression plasmid to introduce the selectable trait allows for the successive introduction of multiple genetic changes into a plant cell by repeatedly using a single standardized selection protocol.

In an alternative embodiment transmutation can be used to introduce a selectable trait. A mixture of a first MDON that causes a selectable mutation in a first target gene and a second MDON that causes a non-selectable mutation in a second target gene is prepared.

One use of this embodiment of the invention is the investigation of the function of a gene-of-interest. A mixture is provided of a MDON that causes a selectable mutation and a MDON that causes a mutation that would be expected to "knock-out" the gene-of-interest, e.g., the insertion of a stop codon or a frameshift mutation. Cells in which one or more copies of the gene-of-interest have been knocked out can be recovered from the population having the selectable mutation. Such cells can be regenerated into a plant so that the function of the gene-of-interest can be determined.

A selectable trait can be caused by any mutation that causes a phenotypic change that can produce a selective growth advantage under the appropriate selective conditions or a phenotypic change that can be readily observed, such as change in color of the plant cells growing in a callus. The selectable trait can itself be a desirable traits, e.g., herbicide resistance, or the selectable trait can be used merely to facilitate the isolation of plants having a non-selectable trait that was introduced by transmutation. A desired nonselectable trait can be introduced into a cell by using a mixture of the MDON that causes the desired mutation and the MDON that causes the selectable mutation, followed by culture under the selecting conditions. Selection according to this scheme has the advantage of ensuring that each selected cell not only received the mixture of MDONs, but also that the cell which received the mixture was then susceptible to transmutation by a MDON.

A mutation that causes a lethal phenotypic change under the appropriate conditions, termed a negatively selectable mutation, can also be used in the present invention. Such mutations cause negatively selectable traits. Negatively selectable traits can be selected by making replica plates of the transmutated cells, selecting one of the replicas and recovering the transmutated cell having the desired property from the non-selected replica.

As used herein a point mutation is mutation that is a substitution of not more than six contiguous nucleotides, preferably not more than three and more preferably one nucleotide. The term point mutation also includes a deletion or insertion of from one to five nucleotides and preferably of one or two nucleotides. As used herein an isolated mutation is a mutation which is not closely linked genetically to any other mutation; mutations that are greater than 100 Kb and preferably greater than 40 Kb and more preferably greater than 23 Kb are not closely linked.

Transmutation of Genes to Create Selectable Traits

The methods of the present invention can be used to transmutate any DNA sequence in a plant, including protein-coding and non-coding sequences. In addition, the target DNA sequence may be one that has previously been introduced into the plant's genetic material and need not be a native plant gene.

According to one embodiment of the invention a MDON is used to introduce a mutation into an acetolactate synthase (ALS) gene, which is also termed the aminohydroxy acid synthase (AHAS) gene. Sulfonylurea herbicides and imidazoline herbicides are inhibitors of the wild-type AHAS enzymes. Dominant mutations that render plants resistant to the actions of sulfonylureas and imidazolines have been described. See U.S. Pat. Nos. 5,013,659 and 5,378,824 (Bedbrook) and Rajasekaran K., et al., 1996, Mol. Breeding. 2, 307-319 (Rajasekaran). Bedbrook at Table 2 describes several mutations (hereafter, a "Bedbrook Mutation") that were found to render yeast ALS enzymes resistant to sulfonylurea herbicides. Bedbrook states that each of the Bedbrook mutations makes a plant resistant to sulfonylurea and imidazoline herbicides when introduced into a plant ALS gene. It is understood that in most plants the gene encoding ALS has been duplicated. A mutation can be introduced into any allele of either ALS gene.

Three of the Bedbrook mutations were, in fact, shown to confer herbicide resistance in a plant, namely the substitutions Pro 196 Ala, Ala 205 Asp and Trp 591 Leu. Rajasekaran reports that mutations Trp 591 Ser caused resistance to sulfonylurea and imidazoline and that Ser 660 Asn caused resistance to imidazoline herbicides. The results of Rajasekaran are reported herein using the sequence numbering of Bedbrook. Those skilled in the art will understand that the ALS genes of different plants are of unequal lengths. For clarity, a numbering system is used in which homologous positions are designated by the same position number in each species. Thus, the designated position of a mutation is determined by the sequence that surrounds it. For example, the mutation Trp591Ser of Rajasekaran is at residue 563 of the cotton ALS gene but is designated as position 591 of Bedbrook because the mutated Trp is surrounded by the sequence that surrounds Trp at position 591 in Table 2 of Bedbrook. According to the invention any substitution for the naturally occurring amino and at position 660 or one of the positions listed in Table 2 of Bedbrook, which is hereby incorporated by reference, can be used to make a selectable mutation in the ALS gene of a plant.

In a further embodiment of the invention the selectable mutation is a mutation in the chloroplast gene psbA that encodes the D1 subunit of photosystem II, see Hirschberg, J., et al., 1984, Z. Naturforsch. 39, 412-420 and Ohad, N., & Hirschberg, J., The Plant Cell 4, 273-282. Hirschberg et al. reports that the mutation Ser264Gly results in resistance to triazine herbicides, e.g., 2-Cl-4-ethylamino-6-isopropylamino-s-triazine (Atrazine). Other mutations in the psbA gene that cause Atrazine herbicide resistance are described in Erickson J. M., et al., 1989; Plant Cell 1, 361-371, (hereafter an "Erickson mutation"), which is hereby incorporated by reference. The use of the selectable trait caused by an Erickson mutation is preferred when it is desired to introduce a second new trait into a chloroplast.

The scientific literature contains reports of other mutations that produce selectable traits. Ghislain M., et al., 1995, The Plant Journal 8, 733-743, describes a Asn104 Ile mutation in the *Nicotiana sylvestris* dihydrodipicolinate synthase (DH-DPS, EC 4.2.1.52) gene that results in resistance to S-(2-aminoethyl)L-cysteine. Mound, G., & King, J., 1995, Plant Physiology 109, 43-52 describes a mutation in the threonine dehydratase of *Arabidopsis thaliana* that results in resistance to L-O-methylthreonine. Nelson, J. A. E., et al., 1994, Mol. Cell. Biol. 14, 4011-4019 describes the substitution of the C-terminal Leu of the S14/rp59 ribosomal protein by Pro, which causes resistance to the translational inhibitors cryptopluerine and emetine. In further embodiments of the invention, each of the foregoing mutations can be used to create a selectable trait. Each of Ghislain, Mourad and Nelson are hereby incorporated by reference.

Producing imidazolinone-resistant *Brassica* species, Rutledge et al. (Mol. Gen. Genet. 229:31-40, 1991) has characterized the AHAS multigene family in *Brassica napus*, which consists of five members. Within this multigene family, AHAS 2, 3, and 4 are associated with the *Brassica campestris* genome (A) and AHAS1 and 5 are associated with the *Brassica oleraceae* genome (C). The *Brassica napus* genome (AC genome combination) is reported to have both AHAS1 and 3 genes.

It is possible to produce plants having mutations in either AHAS1 or AHAS 3, or in both AHAS1 and AHAS 3. It is possible to distinguish mutations in AHAS1 from mutations in AHAS3 using herbicide selection, since mutations in the two genes confer different levels of resistance to imidazolinone herbicides.

Alternatively, *B. campestris* can be used as the starting material, since it has only the AHAS 3 gene. This strategy would ultimately entail the resynthesis of *B. napus* through crosses of *B. campestris* with *B. oleraceae*. Additional breeding would be required to transfer the desired trait into commercial *B. napus* material.

According to one embodiment of the invention, MDON are introduced into *B. napus* by electroporation of microspores with MDON in a low- or no-salt buffer. The haploid nature of microspores and their ability to differentiate directly into embryos and then to plantlets, make them an excellent target tissue source. An important factor for the success of microspore culture is bud selection. If bud selection is precise, large numbers of extremely embryogenic late uninucleate microspores are easily obtained (Fletcher et al., *Double Haploid Technology for Spring and Winter Brassica napus*, OAC Publications, University of Guelph, Canada, 1998). Small germinating embryos or small plantlets produced from unselected microspore populations electroporated with MDON are readily screened for increased herbicide tolerance. Alternatively, the microspores or embryos can be screened using a stepwise selection with imidazolinone herbicide (Swanson et al., Theor. Appl. Genet., 78:525-530, 1989). The availability of the PM1, PM2, and PM1/PM2 resistant mutants allows the performance of reconstruction experiments with mixed microspore populations to design such herbicide screening protocols for MDON-modified *Brassica*.

Mutagenesis Using MDON to Create Desirable Non-Selectable Traits

Any well-known method can be used to screen for a microspore or microspore-derived plant having a desired genetic modification, including, for example, nucleic acid amplification methods such as the polymerase chain reaction (PCR). The gain or loss of a restriction site caused by such gene modification can be assessed by restriction digestion of DNA from a plant followed by Southern blotting and hybridization with an appropriate probe. According to one embodiment of the invention, when the desired mutation is non-selectable, the relevant MDON is be introduced along with a second MDON that introduces a selectable plastid mutation, e.g., a mutation in the psbA gene that confers triazine resistance, or in combination with a linear or circular plasmid that confers a selectable trait. Plants that include the selectable trait arising from the mutagenesis are then screened for the presence of the non-selectable mutation.

EXAMPLES

Example 1

Male Sterility

Certain commercially grown plants are routinely grown from hybrid seed, including corn (maize, *Zea mays*), tomatoes and most other vegetables. The production of hybrid seed requires that plants of one purebred line be pollinated only by pollen from another purebred line, i.e., that there be no self-pollination. The removal of pollen-producing organs from the purebred parental plants is a laborious and expensive process. Therefore, a mutation that induces male-sterility i.e., suppresses pollen production or function, would obviate the need for such process.

Several genes have been identified that are necessary for the maturation or function of pollen but are not essential for other processes of the plant. Chalcone synthase (chs) is the key enzyme in the synthesis of flavonoids, which are pigments found in flowers and pollen. Inhibition of chs by the introduction of a chs antisense expressing gene in the petunia results in male sterility of the plant. Van der Meer, I. M., et al., 1992, The Plant Cell 4, 253-262. There is a family of chs genes in most plants. See, e.g., Koes, R. E., et al., 1989, Plant Mol. Biol. 12, 213-226. Likewise disruption of the chalcone synthase gene in maize by insertion of a transposable element results in male sterility. Coe, E. H., J. Hered. 72, 318-320. The structure of maize chalcone synthase and a duplicate gene, whp, is given in Franken, P., et al., 1991, EMBO J. 10, 2605-2612. Typically in plants each member of a multigene family is expressed only in a limited range of tissues.

Accordingly, the present embodiment of the invention requires that in species having multiple copies of chalcone synthase genes, the particular chs gene or genes expressed in the anthers be identified and interrupted by introduction of a frameshift, and one or more in-frame termination codons or by interruption of the promoter.

A second gene that has been identified as essential for the production of pollen is termed Lat52 in tomato. Muschietti, J., et al., 1994, The Plant Journal 6, 321-338. LAT52 is a secreted glycoprotein that is related to a trypsin inhibitor. Homologs of Lat52 have been identified in maize (termed Zm13, Hanson D. D., et al., 1989 Plant Cell 1, 173-179; Twell D., et al., 1989, Mol. Gen. Genet. 217, 240-245), rice (termed Ps1, Zou J., et al., 1994 Am. J. Bot. 81, 552-561 and olive (termed Ole e I, Villalba, M., et al., 1993, Eur. J. Biochem, 276, 863-869). Accordingly, the present embodiment of the invention provides for a method of obtaining male sterility by the interruption of the Lat52/Zm13 gene or its homologs by the introduction of a frameshift, one or more in-frame termination codons or by interruption of the promoter.

A third gene that has been identified as essential for the production of pollen is the gene that encodes phenylalanine ammonium lyase (PAL, EC 4.3.1.5). PAL is an essential enzyme in the production of both phenylpropanoids and flavonoids. Because phenylpropanoids are a precursor to lignins, which can be an essential for the resistance to disease in the preferred embodiment a PAL isozyme that is expressed only in the anther is identified and interrupted to obtain male sterility.

Example 2

Alteration of Carbohydrate Metabolism of Tubers

Once harvested, potato tubers are subject to disease, shrinkage and sprouting during storage. To avoid these losses the storage temperature is reduced to 35-40° F. However, at reduced temperatures, the starch in the tubers undergoes conversion to sugar, termed "cold sweetening," which reduces the commercial and nutritional value of the tuber. Two enzymes are critical for the cold sweetening process: acid invertase and UDP-glucose pyrophosphorylase. Zrenner, R., et al., 1996, Planta 198, 246-252 and Spychalla, J. P., et al., 1994, J. Plant Physiol. 144, 444-453, respectively. The sequence of potato acid invertase is found in EMBL database Accession No X70368, and the sequence of the potato UDP Glucose pyrophosphorylase is reported by Katsube, T. et al., 1991, Biochem. 30, 8546-8551. Accordingly, the present embodiment of the invention provides for a method of preventing cold sweetening by the interruption of the acid invertase or the UDP glucose phosphorylase gene by introduction of a frameshift, one or more in-frame termination codons or by interruption of the promoter.

Example 3

Reduction in Post-Harvest Browning Due to PPO

Polyphenol oxidase (PPO) is the major cause of enzymatic browning in higher plants. PPO catalyzes the conversion of monophenols to o-diphenols and of o-dihydroxyphenols to o-quinones. The quinone products then polymerize and react with amino acid groups in the cellular proteins, which results in discoloration. The problem of PPO induced browning is routinely addressed by the addition of sulfites to the foods, which has been found to be associated with some possible health risk and consumer aversion. PPO normally functions in the defense of the plant to pathogens or insect pests and hence, is not essential to the viability of the plant. Accordingly, the present embodiment of the invention provides for a method of preventing enzymatic browning by the interruption of the PPO gene by introduction of a frameshift, one or more in-frame termination codons or by interruption of the promoter in apple, grape, avocado, pear and banana.

The number of PPO genes in the genome of a plant is variable; in tomatoes and potatoes PPO forms a multigene family. Newman, S. M., et al., 1993, Plant Mol. Biol. 21, 1035-1051, Hunt M. D., et al., 1993, Plant Mol. Biol. 21, 59-68; Thygesen, P. W., et al., 1995, Plant Physiol. 109, 525-531. The grape contains only a single PPO gene. Dry, I. B., et al. 1994, Plant Mol. Biol., 26, 495-502. When the plant species of interest contains multiple copies of PPO genes it is essential that the PPO gene that is normally expressed in the commercial product be interrupted. For example, only one PPO gene is expressed in potatoes of harvestable size, which gene is termed POT32 and its sequence is deposited in GEN-BANK accession No. U22921. The other potato PPO isozymes have been sequenced and the sequences deposited so that one skilled in the art can design a MDON that specifically inactivates POT32.

Example 4

Reduction of Lignin in Forage Crops and Wood Pulp

Lignin is a complex heterogeneous aromatic polymer, which waterproofs higher plants and strengthens their cell walls. Lignin arises from the random polymerization of free radicals of phenylpropanoid monolignins. Lignins pose a serious problem for the paper industry because their removal from wood pulp involves both monetary and environmental costs. Similarly, the lignin content of forage crops limits their digestibility by ruminants. Indeed, naturally occurring mutations, termed "brown mid-rib" in sorghum, Porter, Kans., et al., 1978, Crop Science 18, 205-218, and maize, Lechtenberg, V. L., et al., 1972, Agron. J. 64, 657-660, have been identified as having reduced lignin content and tested as feed for cattle.

The brown mid-rib mutation in maize involves the O-methyl transferase gene. Vignol, F., et al., 1995, Plant Cell 7, 407-416. The O-methyltransferase genes of a number of plant species have been cloned: Burgos, R. C., et al., 1991, Plant Mal. Biol. 17, 1203-1215 (aspen); Gown, G., et al., 1991, Plant Physiol. 97, 7-14 (alfalfa, *Medicago saliva*) and Jaeck, E., et al., 1992, Mol. Plant-Microbe Interact. 4, 294-300 (tobacco). Thus, one aspect of the present embodiment is the interruption of the O-methyltransferase gene to reproduce a brown mid-rib phenotype in any cultivar of maize or sorghum and in other species of forage crops and in plants intended for the manufacture of wood pulp.

A second gene that is involved in lignin production is the cinnamyl alcohol dehydrogenase (CAD) gene, which has been cloned in tobacco. Knight, M. E., 1992, Plant Mol. Biol. 19, 793-801. Transgenic tobacco plants making a CAD antisense transcript have reduced levels of CAD and also make a lignin that is more readily extractable, apparently due to an increase in the ratio of syringyl to guaiacyl monomers and to the increased incorporation of aldehyde monomers relative to alcohol residues. Halpin, C., et al., 1994, The Plant Journal 6, 339-350. Accordingly, an embodiment of the invention is the interruption of the CAD gene of forage crops such as alfalfa, maize, sorghum and soybean and of paper pulp trees such as short-leaf pine (*Pinus echinata*) long-leaf pine (*Pinus palustris*) slash pine (*Pinus elliottii*), loblolly pine (*Pinus taeda*), yellow-poplar (*Liriodendron tulipifera*) and cotton wood (*Populus* sp.) by introduction of a frameshift, one or more in-frame termination codons or by interruption of the promoter.

Example 5

The Reduction in Unsaturated and Polyunsaturated Lipids in Oil Seeds

The presence of unsaturated fatty acids, e.g., oleic acid, and polyunsaturated fatty acids, e.g., linoleic and linolenic acids, in vegetable oil from oil seeds such as rape, peanut, sunflower and soybean causes the oils to oxidize, on prolonged storage and at high temperatures. Consequently, vegetable oil is frequently hydrogenated. However, chemical hydrogenation causes transhydrogenation, which produces non-naturally occurring stereoisomers, which are believed to be a health risk.

Fatty acid synthesis proceeds by the synthesis of the saturated fatty acid on an acyl carrier protein (ACP) followed by the action of desaturases that remove the hydrogen pairs. Consequently, it would be desirable to inhibit the activity of these desaturase enzymes in oil seeds.

The first enzyme in the synthesis of oleic acid is stearoyl-ACP desaturase (EC 1.14.99.6). The stearoyl-ACP desaturases from safflower and castor bean have been cloned and sequenced. Thompson, G. A., et al., 1991, Proc, Natl. Acad. Sci. 88, 2578-2582; Shanklin, J., & Somerville, C., 1991, Proc. Natl. Acad. Sci. 88, 2510-2514; Knutzon, D. S., et al., 1991, Plant Physiology 96, 344-345. Accordingly, one embodiment of the present invention is the interruption of the stearoyl-ACP desaturase gene of oil seed crops such as soybean, safflower, sunflower, soy, maize and rape by introduction of a frameshift, one or more in-frame termination codons or by interruption of the promoter.

A second enzyme that can be interrupted according to the present invention is ω-3 fatty acid desaturase (ω-3 FAD) the enzyme that converts linoleic acid, a diene, to linolenic acid, a triene. There are two ω-3 FAD isozymes in *Arabidopsis thaliana* and, those skilled in the art expect, in most other plants. One isozyme is specific for plastids and is the relevant isozyme for the synthesis of the storage oils of seeds. The other is microsome specific. The cloning of the *Arabidopsis thaliana* plastid ω-3 FAD is reported by Iba., K. et al., 1993, J. Biol. Chem. 268, 24099-24105. Accordingly an embodiment of the invention is the interruption of the plastid ω-3 FAD gene of oil seed crops such as soybean, safflower, sunflower, soy, maize and rape by introduction of a frameshift, an in-frame termination codon or by interruption of the promoter.

Example 6

Inactivation of S Alleles to Permit Inbred Lines

Certain plant species have developed a mechanism to prevent self-fertilization. En these species, e.g., wheat and rice, one allele of the S locus prevents fertilization by pollen expressing the same S allele (Lee, H-K., et al., 1994, Nature 367, 560-563; Murfett, J., et al., 1994, Nature 367, 563). The product of the S locus is an Rnase (McClure, B. A., et al., 1989, Nature 342, 955-957). The product of the S locus is not essential for the plant. Accordingly, an embodiment of the invention is the interruption of genes of the S locus to permit the inbreeding of the plant by introduction of a frameshift, one or more in-frame termination codons or by interruption of the promoter.

Example 7

Ethylene Insensitivity

Ethylene is a gaseous plant hormone that is involved in plant growth and development. An unwanted aspect of ethylene's action is the over-ripening of fruit, vegetables and the wilting of flowers that results in rotting and loss. The ethylene receptor of *Arabidopsis thaliana* has been cloned and is termed ETR-1 (Chang, C., et al., 1993, Science 262, 539-544). A mutant, Cys65Tyr, results in a dominant insensitivity to ethylene. Transgenic tomato plants expressing the *Arabidopsis thaliana* mutant ETR-1 also showed an insensitivity to ethylene, indicating that the Cys65Tyr mutation would be a dominant suppressor of ethylene action in most plant species. Accordingly one aspect of the present embodiment of the invention is the insertion of the Cys65Tyr mutation into the ETR-1 gene so as to extend the life span of the mutated fruit vegetable or flower.

In a further aspect of the present embodiment, the preservation of the fruit or flower can be achieved by interrupting one of the genes that encode the enzymes for ethylene synthesis: namely 1-aminocyclopropane-1-carboxylic acid synthase (ACC synthase) and ACC oxidase. For this embodiment of the invention the amount of ethylene synthesis can be eliminated entirely, so that ripening is produced by exogenous ethylene or some amount of ethylene production can be retained so that the fruit ripens spontaneously, but a has a prolonged storage life. Accordingly, it is anticipated that the interruption of one allele of either the ACC synthase or the ACC oxidase gene can result in an useful reduction in the level of ethylene synthesis. Alternatively, the invention provides for the interruption of one allele along with the introduction of a mutation that results in a partial loss of activity in the uninterrupted allele.

The sequences of the *Arabidopsis thaliana* ACC synthase and ACC oxidase genes are reported in Abel., S., et al., 1995, J. Biol. Chem. 270, 19093-19099, and Gomez-Lim, M. A., et al., 1993, Gene 134, 217-221, respectively.

Example 8

Reversion of Kanamycin Resistance

Recombinant DNA technology in plants allows for the introduction of genes from one species of plant and bacterial genes into a second species of plant. For example, Kinney, A. J., 1996, Nature Biotech. 14, 946, describes the introduction of a bay laural ACP-thioesterase gene into the rape seed to obtain a vegetable oil rich in lauric acid. Such transgenic plants are normally constructed using an antibiotic resistance gene, e.g., kanamycin resistance, which is coinserted into the transgenic plant as a selectable trait. The resultant transgenic plant continues to express the antibiotic resistance gene, which could result in large amounts of the resistance product and the gene entering the food supply and/or the environment, which introduction may represent an environmental or health risk. An embodiment of the invention obviates the risk by providing for the interruption of the kanamycin gene by introduction of a frameshift, one or more in-frame termination codons or by interruption of the promoter.

Example 9

Modification of Storage Protein Amino Acid Content

Seeds and tubers contain a family of major storage proteins, e.g., patatins in potato and zeins in maize. The amino acid composition of such storage proteins is often poorly suited to the needs of the human and animals that depend on these crops, e.g., corn is deficient in lysine and methionine and potato is deficient in methionine. Accordingly, one embodiment of the invention is the mutation of a storage protein of a food crop to increase the amount of low abundance amino acids. Patatins are encoded by a multigene family which are characterized in Mignery, G. A., et al., 1988, Gene 62, 27-44, and the structure of zeins is reported by Marks, M. D., et al., 1985, J. Biol. Chem. 260, 16451459, both of which are hereby incorporated by reference. Alternatively, the anticodon of a methionine or lysine specific tRNA can be mutated to that of a more common amino acid.

Example 10

The Use of MDON to Determine the Function of a Gene

The presently available techniques for the cloning and sequencing of tissue specific cDNAs allow those skilled in the art to obtain readily the sequences of many genes. There is a relative paucity of techniques for determining the function of these genes. In one embodiment of the invention, MDON are designed to introduce frameshift or stop codons into the gene encoding a cDNA of unknown function. This allows for the specific interruption of the gene, Plants having such specific "knock-outs" can be grown and the effects of the knock-out can be observed in order to investigate the function of the unknown gene.

Example 11

Use of Biolistics to Introduce MDON into a Tobacco (NT-1) Cell Suspension

For microprojectile bombardment of plant cells, the media and protocols found in Gelvin, S. B., et al., (eds) 1991, *Plant Molecular Biology Manual* (Kluwer Acad. Pub.) were followed. Gold particles were coated with MDON according the following protocol. The microprojectiles are first prepared for coating, then immediately coated with the chimeraplast. To prepare the microprojectiles, suspend 60 mg of gold particles in 1 ml of 100% ethanol, Sonicate the suspension for three, 30 s bursts to disperse the particles. Centrifuge at 12,000×g for 30 s, discard supernatant. Add 1 ml of 100% ethanol, vortex for 15 s, centrifuge at 12,000×g for 5 min, then discard the supernatant. A 25 µl suspension of washed gold particles (1.0 µm diameter, 60 mg/ml) in H$_2$O are slowly vortexed, to which 40 µl MDON (50 µg/ml), 75 µl of 2.5 M CaCl$_2$, 75 µl 0.1M spermidine are sequentially added. All solutions are ice cold. The completed mixture is vortexed for a further 10 min and the particles are allowed to settle at room temperature for a further 10 min. The pellet is washed in 100% ethanol and resuspended in 50 µl of absolute ethanol. Biolistic delivery is performed using a Biorad Biolistic gun with the following settings: tank pressure 1100 psi, rupture disks ×2 breaking at 900 psi, particle suspension volume 5 µl.

Lawns of NT-1 of approximately 5 cm in diameter, containing approximately S million cells, were grown for three days on standard media at 28° C. Gold particles were coated with ALS-1 or ALS-2 and were shot as above. The cells were cultured a further 2.5 days, suspended and transferred to solid medium supplemented with 15-50 ppb chlorosulfuron (GLEAN™). Resistant colonies emerged after 7-14 days.

The sequences of the MDON used are as follows: (The nucleotides not homologous with the target gene are underlined and bold. Lower case letters denote 2'-O-methyl ribonucleotides.)

ALS-1
(SEQ ID NO: 1)
5'-CAGGTCAAGTGCAACGTAGGATGATTTTTaucaaccuacGTTGCacu
ugaccugGCGCGTTTTCGCGC-3'

ALS-2
(SEQ ID NO: 2)
5'-CAGGTCAAGTGCTACGTAGGATGATTTTTaucaaccuacGTAGCacu
ugaccugGCGCGTTTTCGCGC-3'

ALS-1 and ALS-2 have single base mismatches with the ALS gene at the second nucleotide of the Pro$^{197}$ (CCA) codon: ALS-1 is CAA and ALS-2 is CTA. Following PCR amplification and sequencing of the gene of the ALS-1 and ALS-2 transmutated, resistant cell lines, a mutation was in the targeted codon which was found to be Thr (ACA) and Ser (TCA), respectively. The observed mutation was shifted one nucleotide 5' of the location that would have been expected based on the action of MDON in mammalian cells on the coding strand and one nucleotide 3' of the expected location on the non-coding strand. A total of 3 ALS-1 and 5 ALS-2 transmutants having these mutations were identified. No resistant calli were obtained from ALS-1 DNA-treated cells.

For selection of chlorsulfuron-resistant cells, cells were transferred from each bombarded plate to 15 ml containing 5 ml of liquid NT-1 cell suspension medium (CSM: Murashige and Skoog salts [Gibco BRL, Grand Island, N.Y.], 500 mg/l MES, 1 mg/l thiamine, 100 mg/l myoinositol, 180 mg/l KH$_2$PO$_4$, 2.21 mg/L 2,4-dichlorophenoxyacetic acid [2,4-D], 30 g/L sucrose, pH 5.7) 2 d after bombardment. The tubes were inverted several times to disperse cell clumps. The cells were then transferred to solidified CSM medium (CSM with add 8 g/l agar-agar [Sigma, St. Louis, Mo.]) containing 15 ppb chorsulfuron (Dupont, Wilmington, Del.). After approximately 3-5 wk, actively growing cells (raised, light-colored colonies) are selected and transferred to solidified CSM containing 50 ppb chlorsulfuron. Three to four weeks later, actively growing cells are selected, then transferred to solidified CSM containing 200 ppb chlorsulfuron. Cells that survive this treatment are then analyzed.

Example 11

Transmutation of GFP in Tobacco Leaf Disks Use of Biolistics to Introduce MDON into a Tobacco (NT-1) Cell Suspension

*Nicotiana tabacum* v. *Samsun* leaf disks were co-transformed by *Agrobacterium tumefaciens* LSA 4404 harboring bin 19-derived plasmids containing a nptII expression cassette containing two genes: a gene for kanamycin resistance and one of two mutants of a gene encoding a Green Fluorescence Protein (GFP, Chui, W., 1996, Current Biol. 6, 325-330). Neither mutant GFP gene produces a GFP product. The mutants contain either a G to T substitution in the sixth codon resulting in a stop codon or a deletion of one nucleotide at the same position, which are termed, respectively, G-stop and G-Δ. After culture on selective MS 104 medium, leaves were recovered and the presence of a GFP gene confirmed by northern blot.

```
Sequence of first eight codons of GFP:
                                      (SEQ ID No. 3)
    GFP ATG GTG AGC AAG GGC GAG GAG CTG
```

The sequences of the MDON used were as follows: (The nucleotides not homologous with G-stop are underlined and bold. Lower case letters denote 2'-Omethyl ribonucleotides.)

```
GFP-1
                                      (SEQ ID NO: 4)
5'-GTGAGCAAGGGCGAGGAGCTGTTCATTTTugaacagcucCTCGCccu ugcucacGCGCGTTTTCGCGC-3'
GFP2
                                      (SEQ ID NO: 5)
5'-TGAGCAAGGGCTCGGAGCTGTTCACTTTTgugaacagcuCCGAGccc uugcucaGCGCGTTTTCGCGC-3'
```

Leaf disks of the G-stop and G-Δ transgenic plants were incubated on MS 104 selective media and G-1 or G-1 introduced biolistically by two successive deliveries as above. Approximately 10 days after the introduction of the MDON, calli exhibiting GFP-like fluorescence were seen in the G-1 and G-2 treated cultures of both the G-stop and G-Δ leaf disks. Larger and more rapidly growing callusing pieces were subdivided by scalpel to obtain green fluorescent cell-enriched calli. The fluorescent phenotype remained stable for the total period of observation, about 30 days. The presence of green fluorescent cells in the G-1 treated G-stop culture indicates that G-1 does not cause mutations exclusively one base 5' of the mismatched nucleotide.

Green fluorescence was observed using a standard FITC filter set using an IMT-2 Olympus microscope.

Example 12

Conversion of GFP in Tobacco Using Electroporation of Mesophyll Protoplasts The plant material used is tobacco plant transformant (Delta6) harboring a deletion mutant of GFP. Leaves were harvested from 5- to 6-week-old in vitro-grown plantlets.

For protoplast isolation, we followed the procedure of Gallois, et al. (1996, Electroporation of tobacco leaf protoplasts using plasmid DNA or total genomic DNA. Methods in Molecular Biology, Vol. 55: Plant Cell Electroporation and Electrofusion Protocols Edited by: J. A. Nickoloff Humana Press Inc., Totowa, N.J. pp. 89-107). The following enzyme solution was used: 1.2% cellulase R-10 "Onozuka" (Karlan, Santa Rosa, Calif.), 0.8% macerozyme R-10 (Karlan, Santa Rosa, Calif.), 90 g/l mannitol, 10 mM MES, filter sterilize, store in 10 ml aliquots at −20° C. Leaves were cut from the mid-vein out every 1-2 mm. They were then placed abaxial side down in contact with 10 ml of enzyme solution in a 100×20 mm petri plate. A total of 1 g of leaves was placed in each plate, and the plates were incubated at 25° C. in the dark for 16 hr. The digested leaf material was pipetted and sieved through a 100 µm nylon screen cloth (Small Parts, Inc., Miami Lakes, Fla.). The filtrate was then transferred to a centrifuge tube, and centrifuged at 1000 rpm for 10 min. All centrifugations for this protocol were done at these conditions. The protoplasts collected in a band at the top. The band of protoplasts was then transferred to a clean centrifuge tube to which 10 ml of a washing solution (0.4 M sucrose and 80 mM KCl) was added. The protoplasts were gently resuspended, centrifuged, then washed again. After the last wash, the protoplast density was determined by dispensing a small aliquot onto a hemocytometer.

For electroporation, the protoplasts are resuspended to a density of $1 \times 10^6$ protoplasts/ml in eletroporation buffer (80 mM KCl, 4 mM $CaCl_2$, 2 mM potassium phosphate, pH 7.2, 8% mannitol, autoclave. The protoplasts were allowed to incubate at 8° C. for 2 hr. After 2 hr, 0.3 ml ($3 \times 10^5$ protoplasts) were transferred to each 0.4 cm cuvette, then placed on ice. GFP-2 (0.6-4 µg/mL) was added to each cuvette except for an unelectroporated control. The protoplasts were electroporated (250V, capacitance 250 µF, and time constant 10-14 ms). The protoplasts were allowed to recover for 10 min on ice, then transferred to petri plates (100×20 mm). After 35 min, 10 ml of POM (80% [v/v] CSM, 0.3M mannitol, 20% [v/v] supernatant from the initial centrifugation of the NT-1 cell suspension prior to protoplast isolation), was added to each plate. The plates were transferred to the dark at 25° C. for 24 hr, then transferred to the light. The protoplast cultures were then maintained according to *Gallois* supra.

Under UV light, we observed 8 GFP converted protoplasts out of $3 \times 10^5$ protoplasts.

Example 12

Canola Microspore Isolation, Electroporation, and Embryogenesis

For microspore isolation, canola (*Brassica napus* or *Brassica rapa*) buds of appropriate size (depending on environmental conditions: 12-20° C., 3.5-4.5 mm; 20-23° C., 3.0-3.5 mm; 23-28° C., 2.2-2.8 mm) are picked from approximately 6-10 racemes for a small culture or up to 50 for a large culture. The buds are then placed in a steel sterilization basket. In the hood, buds are sterilized by submersing the sterilization baskets containing the buds into 200 ml of 5.6% bleach for 10 minutes. The sterile buds are then rinsed with 200 ml of cold, sterile water for 5 minutes, twice. The buds are then transferred from the sterilization baskets to a 12-37 ml capacity blender cup and 25-30 of cold microspore wash (13% sucrose solution, pH 6.0) is added. The buds are homogenized with a blender by alternating high and low speeds, five seconds each, for a total of 20 seconds. (Alternatively, the buds are transferred to the mortar, 30 ml of microspore wash are added, and the tissues are ground up using a pestle for approximately 20 sec.) The contents of the blender cup are poured through nested 63 um and 44 um sterile filters in a beaker-funnel apparatus. The blender cup is then rinsed with 10-15 ml microspore wash. The filtrate is poured into 50 ml plastic centrifuge tubes and the volume is adjusted to 50 ml with microspore wash. The tubes are centrifuged for five minutes at 200×g. After centrifugation, the dark green supernatant is decanted, leaving a yellow spore pellet at the bottom. The wash procedure is repeated two more times for a total of three centrifugations. The supernatant should become clearer with each wash step. The first two cycles of washing should be done in less than 10 minutes to avoid autotoxicity. After the third spin, the microspores are resuspended in 50 ml of NLN liquid culture medium (less NLN can be used, depending on pellet size, to permit an easier volume adjustment after determining initial microspore concentration). To make NLN Medium, combine 0.125 g $KNO_3$, 1.25 g $MgSO_4$ $7H_2O$, 0.5 g $Ca(NO_3)_2$ $4H_2O$, 0.125 g $KH_2PO_4$, and 4 ml $FeSO_4$ EDTA [per 500 ml: 1.39 g $FeSO_4$ $7H_2O$, 1.865 g $Na_2$ EDTA]. Add 10 ml 100×NN vitamin stock [per L: 0.005 g biotin, 0.05 g folic acid, 0.2 g glycine, 10.0 g myoinositol, 0.5 g nicotinic acid, 0.05 g pyridoxine HCl, 0.05 g thiamine HCl], 10 ml 100×MS micronutrient stock [per L: 2.23 g MnSO₄ 4H₂O, 0.62 g boric acid, 0.86 g ZnSO₄.7H₂O, 0.025 g Na₂MoO₄ 2H₂O, 0.0025 g CuSO₄ 5H₂O, 0.0025 g CoCl₂.6H₂O], 0.03 g glutathione [reduced form], 0.8 g L-glutamine, 0.1 g L-serine, 130 g sucrose, and adjust the pH to 6.0.

Electroporation. Microspores are electroporated using the protoplast electroporation procedure detailed above for *Brassica napus* or *Brassica rapa*. For *Brassica* or other species, other well-known microspore electroporation protocols can be used, including those provided by manufacturers for use with electroporation equipment, e.g., the Electro Cell Manipulator® (ECM 600, BTX Division of Genetronics) or Electro Square Porator™ (T820, BTX Division of Genetronics).

For example, for *Zea mays*, the following protocol is provided for use with the Electro Square Porator™ (T820, BTX Division of Genetronics). Pollen is collected from greenhouse-grown plants. Supplemental light is provided by high-pressure 400 W sodium lights with an average output of 500 ft-candles to achieve a 16 hr/daylight period. Tassles are shaken the day before electroporation to remove old pollen and to ensure collection of recently mature pollen the next morning. Pollen is germinated for 3-5 minutes before electroporation in 0.20 M sucrose, 1.27 mM Ca(NO₃)₂ 4H₂O, 0.16 mM H₃BO₃, 0.99 mM KNO₃, pH 5.2. The following electorporation settings are used: HV Mode/3 KV, one pulse of 99 μsec pulse length at a voltage of 1.5 kV and field strength of 3.75 kV/cm using a disposable cuvette (p/n 640) with a 4 mm gap. Electroporation is carried out at room temperature using a sample volume of 800 μl.

Embryogenesis and Regeneration of Plants. The following protocol is employed to achieve embryogenesis of the microspores. A hemacytometer is used to determine the microspore concentration at the initial volume by counting all microspores in each of the corner quadrants of the hemacytometer. The new culture is determined using the following equation: (number of cells counted/number of fields counted) (10,000) (initial volume/100,000)=new volume. The required culture density for microspores is between 80,000 and 100,000 spores per ml. The volume of the culture is adjusted accordingly and the culture is mixed well. 15 ml of the culture is pipetted into an appropriate number of petri plates. For even plating, one can make slight adjustments (usually no more than 2-3 ml) to make the culture volume a factor of 15, resulting in even plating. Plates are sealed with a double layer of parafilm and stacked in a 30° C. incubator in the dark. After seven days, the plates are observed under an inverted scope to look for cell divisions and embryo development. If cell divisions and tiny globular embryos are observed, the plates are returned to the incubator for another seven days. Otherwise, the culture is discarded. After 14 days at 30 C, the plates are placed on a shaker at 50 rpm at room temperature in the dark for an additional 14 days. After 28-35 days of culture, embryos should be approximately 5 mm long with visible cotyledons. Embryos are then transferred to solid B5 germination medium and exposed to a temperature of 4° C. immediately after transfer to solid medium to increase the yield of mature embryos. To make B5 solid germination medium, combine 400 ml B5×10 Stock (per 4 L: 50 g KNO₃, 5 g MgSO₄ 7H₂O, 15 g CaCl₂ 2H₂O, 2.68 g (NH₄)₂SO₄, 3 g NaH₂PO₄ H₂O, 32 ml FeSO₄ EDTA), 200 ml B5 vitamin stock [per L: 10 g myoinositol, 0.1 g nicotinic acid, 0.1 g pyridoxine HCl, 1 g thiamine-HCl], 200 ml 100×B5 micronutrient stock [per L: 1 g MnSO₄ H₂O, 0.3 g H₃BO₃, 0.2 g ZnSO₄ 7H₂O, 0.025 g Na₂MoO₄ 2H₂O, 0.0025 g CuSO₄ 5H₂O, 0.0025 g CoCl₂ 6H₂O], 20 ml KI stock [0.83 g/L KI]; 40 g sucrose; and 2 ml GA₃ stock [0.1 g/L GA]. Bring the volume up to 2 L with double distilled water, pH 5.7, and add 8 g agar per L before autoclaving. The embryos are maintained at 4° C. for 10 days. The plates are then moved to a light chamber set between 23 and 27° C. with a 12 hr light regime. The plates remain in these conditions for 30 days. The plantlets generated after this period can be transferred directly to soil.

The following MDON are useful for introducing desirable mutations into target DNA sequences, for example in Brassicaceae such as canola:

A. Tobacco Acetolactate Synthase

ALS1 (SEQ ID NO: 6):
5'-CAGGTCAAGTGCAACGTAGGATGATTTTTaucauccuacGTTGCacu ugaccugGCGCGTTTTCGCGC-3'

ALS2 (SEO ID NO: 7):
5'-CAGGTCAAGTGCTACGTAGGATGATTTTTaucauccuacGTAGCacu ugaccugGCGCGTTTTCGCGC-3'

B. Tobacco Green Fluorescent Protein
Note:      WT           GGC GAG GAG

MutantD6     GGG -AG-GAG

MutantSTOP   GGC TAG GAG

GFP1 (SEQ ID NO:8)—Works on mutantD6 and mutantSTOP, Restoring Wild-Type Activity 5'-GTGAGCAAGGGCGAGGAGCTGTTCATTTTugaacagcucCTCGCccu ugcucacGCGCGTTTTCGCGC-3'

GFP2 (SEQ ID NO:9)—Works on mutantSTOP, Restoring Wild-Type Activity

5'-TGAGCAAGGGCTCGGAGCTGTTCACTTTTgugaacagcuCCGAGccc uugcucaGCGCGTTTTCGCGC-3'

C. *Arabidopsis thaliana* Phosphoribosylanthranilate Transferase

PAT4 (SEQ ID NO:10)—Mutant to Wild-Type: AAT to AGT (Asparagine to Serine)

5'-CTGCTTGTGGAAGTGCTGATGTACTTTTTaguacaucagCACTTcca caagcagGCGCGTTTTCGCGC-3'

PAT3 (SEQ ID NO:11)—Wild-Type to Mutant: AGT to AAT (Serine to Asparagine)

5'-CTGCTTGTGGAAATGCTGATGTACTTTTTaguacaucagCATTTcca caagcagGCGCGTTTTCGCGC-3'

D. *Arabidopsis thaliana* Fatty Acid Desaturase

ATFAD2/217 (SEQ ID NO:12)—Introduces a Stop Codon into the Wild-Type Sequence (CCC ATC TAC AAT GAC to CCC ATC TAG AAT GAC)

5'-CGCTCCCATCTAGAATGACCGAGAATTTTuucucggucaTTCTAgau gggagcgGCGCGTTTTCGCGC-3'

E. Tobacco Putrescine N-Methyltransferase (SEQ ID NO:13)

5'-AATGGCACTTCTTAACACCTCAACGTTTTcguugaggugTTAAGaag ugccauuGCGCGTTTTCGCGC-3'

F. Canola AHAS3 Gene—S635N (AGT to AAT) (SEQ ID NO:14)

5'-CGATGATCCCAAGTGGTGGCACTTTTTTTaaagugccacCACTTggg aucaucgGCGCGTTTTCGCGC-3'

We claim:

1. A plant microspore comprising a mixed duplex oligonucleotide.

2. The plant microspore composition of claim 1, wherein the plant is a member of the family Brassicaceae.

3. The plant microspore composition of claim 2, wherein the plant microspore is a *Brassica napus, Brassica rapa, Brassica olercea* or a *Brassica juncea* microspore.

4. A composition comprising:
   a. a plant microspore and
   b. a mixed duplex oligonucleotide inside the plant microspore wherein the mixed duplex oligonucleotide is capable of causing a genomic mutation in the microspore.

5. The composition of claim 4 wherein the microspore is from a plant of the family Brassicacaea.

6. The composition of claim 5, wherein the plant microspore is a *Brassica napus, Brassica rapa, Brassica oleracea* or *Brassica juncea* microspore.

* * * * *